(12) United States Patent
Eaton

(10) Patent No.: US 10,653,054 B2
(45) Date of Patent: May 19, 2020

(54) METHOD FOR PRODUCING A BIODIGESTER REACTOR AND MEMBRANE TEMPLATE

(71) Applicant: BUEN MANEJO DEL CAMPO, S.A. DE C.V., Mexico City (MX)

(72) Inventor: Alexander Bennet Eaton, Mexico City (MX)

(73) Assignee: BUEN MANEJO DEL CAMPO, S.A. DE C.V., Mexico (MX)

( * ) Notice: Subject to any disclaimer, the term of this patent is extended or adjusted under 35 U.S.C. 154(b) by 0 days.

(21) Appl. No.: 16/469,335

(22) PCT Filed: Sep. 21, 2018

(86) PCT No.: PCT/MX2018/050022
§ 371 (c)(1),
(2) Date: Jun. 13, 2019

(87) PCT Pub. No.: WO2019/088818
PCT Pub. Date: May 9, 2019

(65) Prior Publication Data
US 2019/0380258 A1    Dec. 19, 2019

(30) Foreign Application Priority Data

Nov. 1, 2017 (MX) .................... MX/a/2017/014024

(51) Int. Cl.
| | |
|---|---|
| *A01C 3/02* | (2006.01) |
| *C12M 1/107* | (2006.01) |
| *C12M 1/00* | (2006.01) |
| *C12M 1/12* | (2006.01) |

(52) U.S. Cl.
CPC ............. *A01C 3/023* (2013.01); *C12M 21/04* (2013.01); *C12M 23/06* (2013.01)

(58) Field of Classification Search
CPC ........ A01C 3/023; C12M 23/06; C12M 21/04
See application file for complete search history.

(56) References Cited

U.S. PATENT DOCUMENTS

| | | |
|---|---|---|
| 3,356,120 A | 12/1967 | Nohmura |
| 3,962,959 A | 6/1976 | Williamson |
| 4,100,023 A | 7/1978 | McDonald |

(Continued)

FOREIGN PATENT DOCUMENTS

WO    WO2011133023 A1    10/2011

OTHER PUBLICATIONS

Davis, C.H. & Preston, T. R. A combined digester and gasholder PVC plastic tube biogas unit. ADAS News, 1983. [online] [webpage]. [ recovered Dec. 2, 2018]. Recovered from <http://www.fastonline.org/CD3WD _ 40/JF/JF OTHER/SMAL L/Low-cost%20plastic%20biodigesters%20-%20Davis%20& %20Preston. pdf>.

(Continued)

*Primary Examiner* — John C Hong
(74) *Attorney, Agent, or Firm* — Berenato & White, LLC

(57) ABSTRACT

Methods, systems and/or apparatus related to the manufacture and use of biodigesters are disclosed. Moreover, techniques for the manufacture of reactors whose final shape increases the lifespan of the biodigester, as well as modular techniques for the manufacture of the reactors, are included.

16 Claims, 6 Drawing Sheets

(56) References Cited

U.S. PATENT DOCUMENTS

| | | | |
|---|---|---|---|
| 4,579,654 A | 4/1986 | Bremmer | |
| 5,151,076 A | 9/1992 | Strand | |
| 6,451,206 B1 * | 9/2002 | Charbonneau | C12M 21/04 210/170.09 |
| 6,855,253 B2 * | 2/2005 | Baumgartner | C02F 3/28 210/603 |
| 7,320,753 B2 * | 1/2008 | Roos | A01C 3/023 210/603 |
| 7,883,884 B2 * | 2/2011 | Bonde | A01C 3/00 435/236 |
| 2002/0148401 A1 | 10/2002 | Eagles et al. | |

OTHER PUBLICATIONS

House, D. How to build a plastic bag digester. The complete Biagas Handbook, Jun. 22, 2016. [online ] [webpage]. (recovered on Dec. 2, 2018]. recovered from <https://completebiogas.com/b_plastic.html>.

* cited by examiner

METHOD FOR PRODUCING A BIODIGESTER REACTOR AND MEMBRANE TEMPLATE

CROSS-REFERENCE TO RELATED APPLICATIONS AND CLAIM TO PRIORITY

This application is a national stage application of International Application No. PCT/MX2018/050022 filed Sep. 21, 2018, which claims priority to Mexican Patent Application No. MX/a/2017/014024 filed Nov. 1, 2017, the disclosures of which are incorporated herein by reference and to which priority is claimed.

FIELD OF THE INVENTION

The present invention relates generally to the field of biodigester systems, and more specifically, to a biodigester system including a reactor whose method of manufacture provides a longer lifespan than the average found in the art. The biodigester system includes, among others, an inlet, a reactor, and an outlet, wherein said biodigester system produces fertilizer and gas conditioned for domestic use. The biodigester system includes methods of manufacturing and using the same.

BACKGROUND OF THE INVENTION

Biodigester systems are widely known in the art. Thousands of years ago, man found that it is possible to obtain methane gas, also called as biogas, and a potent organic fertilizer, also called as biol, from organic matter (cattle feces, human feces, blended fruits and vegetables, etc.) through its fermentation with anaerobic bacteria. In its simplest form, a biodigester system is a hermetically or tightly sealed container (also called anaerobic reactor or bag), within which said organic matter is stored, wherein said biodigester system further includes a certain mixture with non-potable water, so that the organic matter fermentation with anaerobic bacteria may produce said biogas and biol, thereby reducing the contaminating potential of feces, the attraction of insects, the generation of germs, and odors.

Biogas is a fuel capable of substituting fossil fuels or biomass (firewood). Biogas is produced from the decomposition of the organic matter, also called biomass, in a humid environment free of oxygen, by means of the bacteriological activity. Biogas is composed of approximately 60% methane ($CH_4$) and 40% carbon dioxide ($CO_2$). Biogas contains minimum amounts of other gases, including water ($H_2O$) and sulfhydric acid ($H_2S$). Biogas is somewhat lighter than air and has an ignition temperature of approximately 700° C., its flame reaches a temperature of 870° C., and it can be used as a fuel when the concentrations of methane are greater than or equal to 50%, as biomass has a high calorific value.

Biol is a liquid organic fertilizer produced from the decomposition of organic matter, such as animal manure, green plants, fruits, among others, in the absence of oxygen. Biol contains nutrients which are easily assimilated by plants, thus making them more vigorous and resistant. The technique employed to obtain biol is through biodigesters.

A common biodigester system is comprised by a reactor defined by a sealed bag storing the manure and/or organic waste, hereinafter called organic matter, for a period of time. Said reactor causes the biogas produced from decomposition to be stored and channeled for using the same. The common reactor is usually installed within a ditch at least partially enclosing said reactor by the ditch walls. The reactor includes an inlet whereby the organic matter enters the reactor, a biol outlet, and a biogas outlet whereby said biogas is channeled. The inlet and the outlet are usually sealed with a water seal. Due to the biogas density, the biogas outlet is usually located at the upper part of the reactor. The product obtained at each of the outlets is used, since biogas may be used as a fuel, and the biol is used as an organic fertilizer.

The technique to build the reactor has changed very little since the first biodigester systems were developed, changing only the membrane-type material used for manufacturing said reactor. At present, given its availability, it is common to use PVC as a manufacturing material for the reactor, since PVC is easy to get at an affordable price. In this regard, it is already known in the art that a direct contact with the sun's rays accelerates the manure decomposition process. However, PVC undergoes a short-term degradation as a result of said sunrays, so users cover the reactors, or create a sort of greenhouse for said reactors, thereby reducing the efficiency and increasing the implementation cost for biodigesters manufactured with PVC.

In the art, one way of manufacturing a reactor is by using two templates of impermeable material or membrane, with one template being an upper template and the other template being a lower template, wherein said templates have the same shape, usually an oval or circular shape. Thus, the upper template is placed on top of the lower template and said templates are joined together by sealing the templates at their contours or perimeters, defining a body whose interior may be inflated, forming a balloon (wherein said balloon takes the shape of the templates) for the subsequent introduction of the organic matter and/or the obtaining of biol through orifices with predefined dimensions. Another way known in the art of manufacturing a reactor is from three templates. The first template being a rectangular template forming a sleeve or pipe when the template longest parallel sides are joined together, said pipe being sealed by using at each end a circular template with a diameter that is equal to the diameter of said pipe. Therefore, in the end, when the reactor is inflated, the reactor design resembles that of a sausage.

In this regard, certain advantages have been found in the reactors manufactured from simple-shaped templates, i.e. from the joining of rectangular, circular, oval, or similar templates, because, when the organic matter is introduced and biogas starts to be produced, i.e. the heaviest liquid matter being at the lower part and the gas being at the upper part, said reactor inflates, thus generating different efforts and forming a plurality of creases in its perimeter or usually at the zones where the template joining is performed. The reactor surface where said creases are located is subjected to a plurality of undesired efforts on the material, since said zones will eventually exhibit leakages or tears, thus reducing the reactor lifespan, and representing a risk to users. Also, such creases may not be prevented even after the maximum inflation of the reactor, since this only increases the undesired efforts on the material, i.e. the creases remain, but said creases exert greater efforts on the material.

Therefore, it is desirable to obtain a biodigester system in which the reactor shape, when inflated, prevents the creation of creases and fits the content including substances of different densities.

Furthermore, it is desirable that said reactor is manufactured with a material that meets the characteristics of efforts, and that is also resistant to solar radiation.

In this regard, it has been found that the biogas thus obtained cannot be directly used by a user, since this gas contains hydrogen sulfide, which is highly corrosive and has significant amounts of water. Therefore, it is also desirable to obtain a biodigester system that includes filtrating and/or refining processes so that biogas can be used immediately.

It has also been found that there is a need to manufacture biodigester systems with different dimensions and capacities, wherein there is a direct relationship between the biodigester system size and the biodigester system biogas or biol production capacity. However, this variation in the user's needs makes it difficult to manufacture a standardized biodigester system, since several square meters of membrane are needed to manufacture a standard biodigester system. In this regard, it has been found that the users' needs change with time, and in certain cases this results in the user requiring to expand its biodigester system and also to expand the biodigester system capacities, including the land area required and the respective ditch. However, the technique currently used for the manufacture of biodigester systems does not allow for such expansion. Therefore, it is desirable a biodigester system which provides or not for the use of ditches to enclose the biodigester system reactor, thereby facilitating the implementation thereof, and which also provides for the use of interconnections between reactors to modularly expand the capacity of the original biodigester system. Thus, it is desirable to design a modular biodigester system whose manufacturing complexity does not rely on the size of said biodigester system and allows for future expansions, wherein the interconnection between different biodigesters is simple and provides an increase in the production of biogas and/or biol.

Finally, it is desirable to design a biodigester system which covers all the stages of the process, from the introduction of manure to the obtaining of biol or biogas, directly applied either to a stove, internal combustion engine or any other apparatus having the capacity to operate with said fuel.

SUMMARY OF THE INVENTION

The present invention relates to methods, systems, devices and/or apparatuses related to biodigesters and/or the manufacturing of biodigesters. The biodigester system including a reactor; an inlet connected to said reactor; an outlet connected to said reactor; a reactor biogas outlet; a pressure relief valve; a filter for reducing hydrogen sulfide; a protection textile; and/or a water trap. In an embodiment of the invention, the material used for the manufacture of the inlet the reactor, and/or the outlet, is a geomembrane or also called membrane. Said membrane is selected from the list of: high- or low-density polyethylene, high- or low-density polypropylene, bituminous elastomer, or polyvinyl chloride. The techniques shown herein may be applied to the manufacturing of any type of sealed bag containing one or more types of fluids, preferably low-pressure fluids.

The reactor includes at least one inlet orifice and at least one outlet orifice. In an embodiment of the invention, the reactor is connected to the inlet and/or to the outlet through an inlet orifice and an outlet orifice, respectively, by using a piping system. In an embodiment of the invention, said piping system is a PVC or similar piping system. Moreover, in an embodiment of the invention, the way in which the piping system is attached to each orifice is by means of a flange. In an embodiment of the invention, said flange is composed of two elements attached to each other by means of a screw/nut relationship, wherein the shape of said elements allows to trap the geomembrane material located around each orifice, pressing it as the screw/nut is applied, and to connect each piping system as well. Furthermore, each element of the flange includes a gasket made of an impermeable resilient material, such as rubber or any other similar material which prevents fluid leakages. Each flange is coupled either at the connection of the inlet and/or at the connection of the outlet manhole.

In an embodiment of the invention, the reactor gas outlet includes a flange and a biogas piping system, wherein a pressure relief valve is coupled and said pressure relief valve includes a bypass valve. Additionally, the biogas piping system includes a water trap and/or a filter for reducing the amount of hydrogen sulfide found in the biogas thus obtained. In an embodiment of the invention, the filtering material is any ferrous material.

In a further embodiment of the invention, the filtering material may include natural fibers such as coconut fibers, the composition of which allows for a chemical reaction to extract hydrogen sulfide from the biogas exiting the reactor.

In an embodiment of the invention, the reactor is manufactured from a single substantially rectangular membrane template, or also called rectangular membrane, to which cuts are made for the removal of quadrilateral-shaped membrane segments at each rectangle distal end; that is, on the rectangle smallest sides. In this regard, the substantially rectangular membrane template is joined at each end of its longest sides, thereby forming a sleeve, cylinder or pipe.

Those skilled in the art will appreciate that the location of the quadrilateral-shaped cuts may be made on the rectangle smallest sides or on the rectangle longest sides without affecting the subject matter of the present invention.

In a particular embodiment of the invention, the quadrilaterals are rectangular in shape. In another particular embodiment of the invention, the quadrilaterals have the shape of a rectangular trapeze. In a further embodiment of the invention, the quadrilaterals are trapezoidal and rectangular in shape. In this regard, a trapeze is defined by a quadrilateral having two non-consecutive parallel sides called the trapeze bases, wherein the mean distance between said parallel sides will be called mean.

Therefore, when each opposite end of the rectangular membrane is cut, or when two segments with a quadrilateral shape are removed from the membrane and the two remaining opposite ends of the rectangular membrane are joined together forming a sleeve, a sleeve with cuts at its ends is obtained, said sleeve will be called cut sleeve. From said cut sleeve, it is possible to obtain the reactor of the present invention.

In an embodiment of the invention, a technique for the manufacture of a modular reactor is disclosed, wherein the rectangular membrane template is divided into a segment corresponding to the body (with a shape of simple pipe or cylinder) and segments corresponding to the ends (with a particular shape using the technique which prevents the creation of creases). Therefore, each end segment forms each reactor end, and another body segment forms the reactor body. Since the body diameter corresponds to the diameter of the ends, by keeping said diameter the body may vary in length, thus varying the reactor capacity, such that when each end segment is joined to the reactor body segment, the final reactor is defined. In an embodiment of the invention, the shape and dimensions of each reactor end segment template and reactor body segment template may vary without affecting the subject matter of the present invention. Therefore, it is possible to increase or decrease the capacity of each biodigester system simply by modifying the particular template corresponding to the reactor body segment. In an embodiment of the invention, said particular reactor template is a simple rectangular template.

In an embodiment of the invention, the biodigester system includes a low-pressure gas adapter that allows coupling an apparatus or compatible gas burner device to the biogas line. Examples of gas burner apparatuses or devices include stoves, heaters, engines, etc.

Furthermore, in an embodiment of the invention, the system of the present invention includes a mixer coupled to a common fuel engine, such that biogas serves as a fuel for said engine. In this regard, the adapter helps the biogas be compatible with said engine, thus skipping stages of the internal combustion so that biogas is injected directly in the non-liquid stage of the internal combustion and then be burned in its gaseous form.

DETAILED DESCRIPTION OF THE INVENTION

The following description is provided to enable those skilled in the art to make and use the embodiments, and said description is provided within the context of a particular application and the requirements thereof. Various modifications to the embodiments disclosed herein will become easily evident to those skilled in the art and the general principles defined herein may be applied to other embodiments and applications without departing from the spirit and scope of the present disclosure. Therefore, the present invention is not limited to the embodiments shown, but on the contrary, the present invention must conform to the widest scope consistent with the principles and characteristics disclosed herein.

Figure 1:
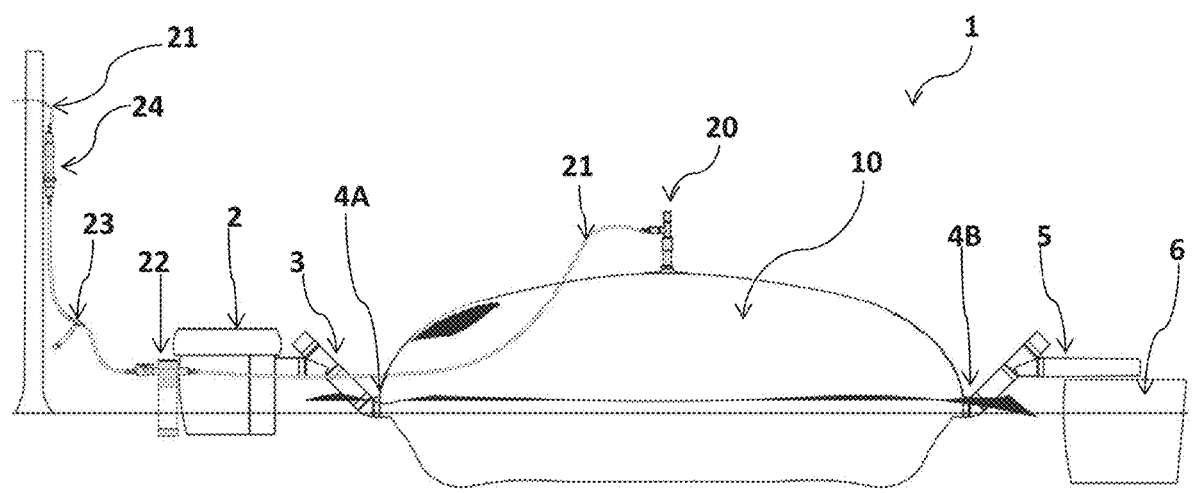
FIG. 1 shows one embodiment of the biodigester system of the present invention.

FIG. 1 shows an embodiment of the biodigester system 1 of the present invention, wherein said system 1 includes a reactor 10, a biogas outlet 20, a gas piping 21, an inlet flange 4A, an inlet piping 3, an inlet 2, an outlet flange 4B, an outlet piping 5, an outlet 6, a pressure relief valve 22, a water trap 23, and a hydrogen sulfide filter 24, also called as sulfhydric acid in dissolution, wherein the valve 22, the trap 23, and the filter are coupled to the biogas piping 21.

In an embodiment of the invention, the reactor 10, the inlet 2, and the outlet 6 are manufactured with the same membrane material. In an embodiment of the invention, the material used for the manufacture of said elements 10, 2, and 6 is selected from the list of: high- or low-density polyethylene, high- or low-density polypropylene, bituminous elastomer, or polyvinyl chloride.

The organic matter mixed with water is introduced in the reactor 10 through the inlet 2 and the piping 3. In this regard, there is a difference in heights between said inlet 2 and the reactor 10 so that a water seal is formed to prevent the organic matter from returning to the inlet 2.

Once biogas starts to be produced, the biogas comes out through the outlet piping 5 to be collected in the outlet 6. In this regard, the biogas coming out through the gas outlet 20 is then channeled by a piping 21 to a certain apparatus or device wherein said gas can be used as a fuel. In order for the biogas to reach suitable conditions for use, said biogas is firstly passed through a pressure relief valve 22 and a water trap 23, and through a filter 24 which removes hydron sulfide from the biogas.

Figure 2:
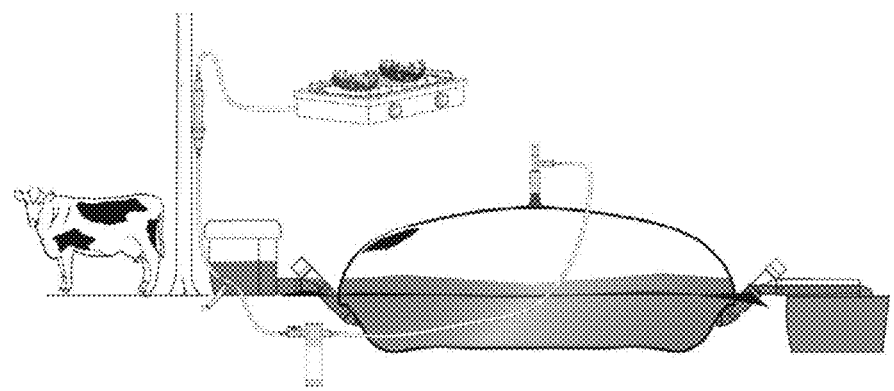
FIG. 2 shows a reference image of the biodigester system of the present invention, wherein a stove fed with biogas is included.

FIG. 2 depicts a reference image of a biodigester system such as that of an embodiment of the present invention, showing the organic matter from the inlet, passing through the reactor, wherein biogas is produced, and moving to the outlet already converted to biol. The biogas is channeled, for example, to a stove for use thereof, wherein said channeling includes a pressure relief valve, a water trap, and a hydrogen sulfide filter.

Figure 3:
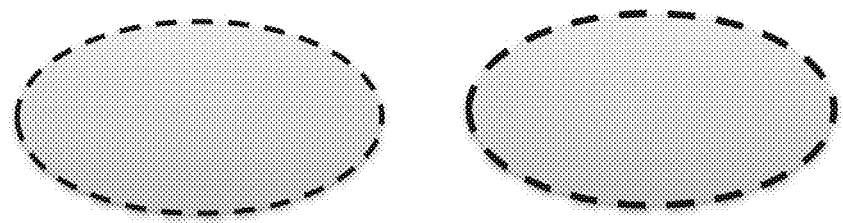
FIG. 3 shows one example of simple templates used for the manufacture of reactors in the previous art.

FIG. 3 shows an example of two simple templates used for the manufacture of the reactors of the previous art, wherein said templates form the reactor when said templates are placed one on top of the other and are joined together at its perimeters. However, this manufacturing technique causes a plurality of undesired creases to be created along the joining line between the two templates.

Figure 4:
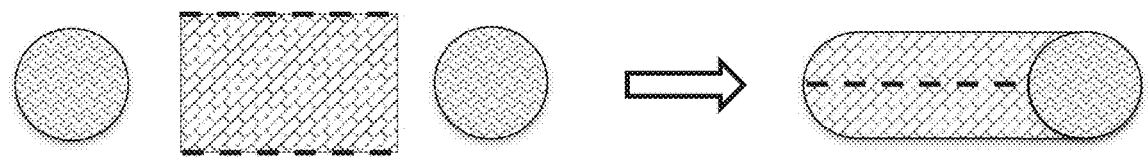
FIG. 4 shows another example of the manufacture of the reactor from simple templates, a rectangle and a circle in this case.

FIG. 4 shows another example of a reactor manufactured by employing the techniques customary in the art, using a rectangular template and two circular templates. Thus, from the rectangular template, a sleeve or cylinder is formed when two of the template ends are joined together (ends shown in dashed lines), wherein said sleeve has a diameter corresponding to the original dimensions of the rectangle, i.e. wherein the perimeter of the circular opening of the sleeve or pipe is the same as the length of the width of the original rectangular template. Those skilled in the art will appreciate that from known mathematical calculations it is possible to determine the dimensions of the circular templates and/or of the final reactor. The circular template has a diameter corresponding to the diameter of the sleeve, such that each circular template works as a sleeve cap (on both sides of the sleeve), thereby defining a reactor, wherein the length of said reactor is usually defined by the dimensions of the rectangular template. In this regard, it has been found that this technique for the manufacture of reactors causes undesired efforts on the distal ends of the reactor, i.e. creases are created along the template joining line, thus reducing the lifespan of the biodigester system.

Figure 5:
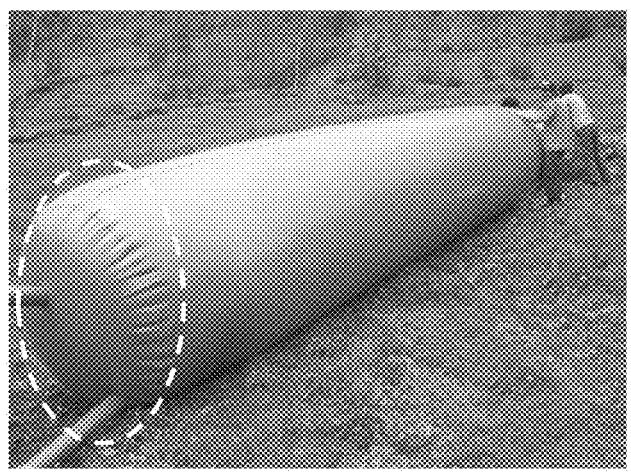
FIG. 5 shows an image of the creases in a reactor of the previous art using the technique of FIG. 4.

FIG. 5 shows an example of the creases created on the template joining line, said creases generating undesired efforts on the reactor material. In this regard, the material is subjected to a series of efforts on said zone of creases which subsequently result in breaks or leakages, since these zones exhibit a greater wear, thus reducing the lifespan of the reactor and representing a risk to users.

Figure 6:
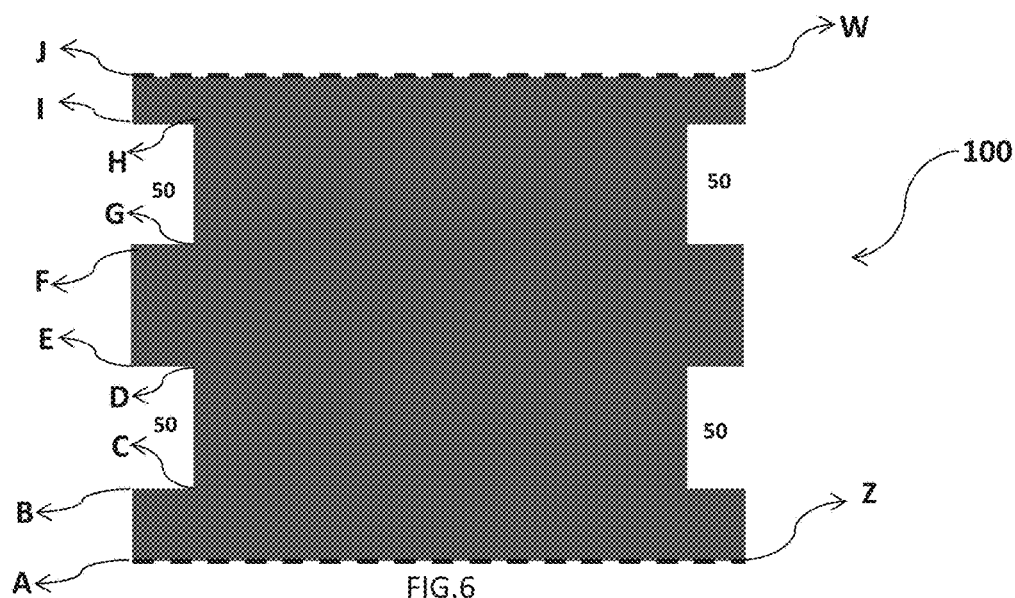
FIG. 6 shows a template used for the manufacture of a reactor without creases in accordance with an embodiment of the present invention, wherein the cuts for the removal of rectangular shapes on each side of said template can be observed.

FIG. 6 shows an embodiment of the present invention disclosing a template 100 used to form, from different joins and/or folds, a reactor which prevents the creation of creases. Said FIG. 6 shows an example deformed from its accurate scaled dimensions for illustrative purposes. The template is formed from a membrane rectangle AJWZ, wherein cuts BCDE and FGHI are made for the removal of quadrilaterals 50, said cuts are symmetrically made on both sides of the template 100 (left and right in accordance with the orientation of FIG. 6); however, for illustrative purposes, reference is made only to the cuts corresponding to the left side of the template 100. Therefore, when the template is joined at the template longest edge (dashed lines), a sleeve including said cuts is formed, and when said cuts are joined together in a certain way, a bag is created, so that when said bag is inflated, this prevents the creation of creases such as those found in the art. In an embodiment of the invention, the magnitudes of the cuts BCDE and FGHI (and its corresponding counterparts on the right side) vary depending on the dimensions of the rectangle AJWZ, and on the mechanical properties of the membrane material, such as the dimensions, thickness, resilient properties, and on the capacity sought for the reactor, etc. For example, it is complicated for a manufacturer to make the respective folds on a membrane material of 6 mm thick than the folds on a same material of 3 mm thick. Said folds include folds for the manufacture of the reactor and/or for the transportation of the reactor, since said reactor must be deflated, folded and transported, or dismantled so as to occupy the least space possible in the transportation means.

In this regard, the mechanical properties also include features such as resilient properties of the material, thermal properties of the material, etc.

Distance EF results from the sum of distances AB+IJ. Distance AB and distance IJ may or may not be the same.

Thus, the joining of the longest edges of the template or of the rectangle AJWZ (dashed line) forms a sleeve including the cuts previously defined, such that elements AB and IJ, when joined together, form the element BI.

In an embodiment of the invention (not shown in the figures), the rectangle formed by points DEFG is cut to form a rectangle with a smaller projection relative to the template body.

In this regard, a method of joining the edges of template 100 is included, said method includes the steps of:
joining element EF to element BI, wherein point B is in direct contact with point E, and point F is in contact with point I;
joining element CD to elements DE and BC accordingly;
joining element GH to elements FG and HI accordingly;
Those skilled in the art will appreciate that said method may also be applied to the right counterpart of template 100.

Moreover, those skilled in the art will appreciate that there are different techniques for making the cuts in rectangle AJWZ to form the respective template, without affecting the subject matter of the present invention.

In an embodiment of the invention, the cuts are made after having formed the sleeve, defined by the joining of the longest ends AZ and JW of said rectangle AJWZ.

Figure 7:
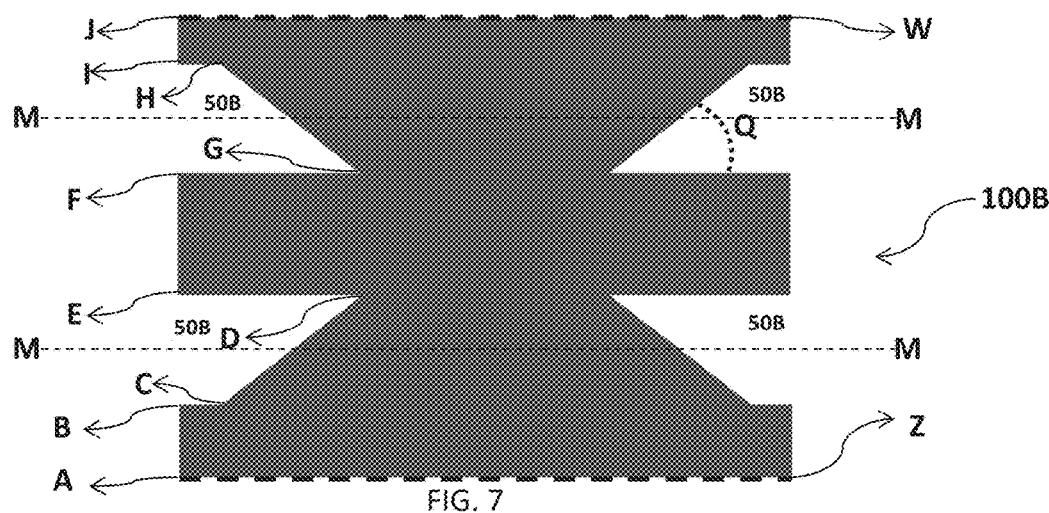
FIG. 7 shows a template used for the manufacture of a reactor without creases in accordance with another embodiment of the present invention, wherein the cuts for the removal of trapeze-type shapes on each side of said template can be observed, and wherein the trapeze mean defined by the mean distance between the trapeze parallel sides can also be observed.

FIG. 7 shows an embodiment of the present invention disclosing a template 100B for the manufacture of a biodigester system reactor, wherein said reactor will have an angled shape. Thus, the shown cuts BCDE and FGHI (including the respective cuts not shown in the figures on the right side of the template) are made in a membrane rectangle AJWZ to form the quadrilaterals 50B, including cuts with non-straight angles Q. Said non-straight angle may vary according to the final capacity of the biodigester, the mechanical properties of the membrane material, the place at which said biodigester is installed, the use or non-use of ditches, and any other factor. In an embodiment of the invention, the dimensions of said cuts and of said angle may vary depending on the original dimensions of rectangle AJWZ and on the final shape sought for the reactor. In this regard, the reactor takes a wider shape at the lower part (relative to the upper or opposite part) as angle Q approaches to 0° in order to more evenly withstand the efforts generated by the accumulation of liquid and more dense waste at the lower part of the reactor. In this regard, this technique also provides for the implementation of biodigester systems 1 which prevent the use of ditches to enclose the reactor.

Distance EF results from the sum of distances AB+IJ. Distance AB and distance IJ may or may not be the same.

Thus, the joining of the longest edges of the template or of the rectangle AJWZ (dashed line), forms a sleeve including the cuts previously defined, such that elements AB and IJ, after said joining, become the element BI.

Moreover, FIG. 7 shows the quadrilateral middle lines 50 along which sleeve folds are made. Thus, once the membrane sleeve is folded on the quadrilateral middle lines, said quadrilaterals may be joined together to form the crease-preventing reactor.

In this regard, a method of joining the edges of template 100B is included, said method includes the steps of:
for the lower left quadrilateral:
forming a sleeve by joining line AZ to line JW;
joining line CD to adjacent line DE, partially sealing the sleeve;
joining line EF to line AB+IJ, accordingly;
Those skilled in the art will appreciate that said method may also be applied to each quadrilateral of template 100B. Moreover, those skilled in the art will appreciate that there are different techniques for making the cuts for the removal of quadrilaterals 50B. In this regard, in an embodiment of the invention, said cuts are made before forming the sleeve. In a further embodiment of the invention, said cuts are made after forming the sleeve.

In an embodiment of the invention, the rectangle formed by points DEFG is cut to form a rectangle with a smaller projection relative to the template body. In an embodiment of the invention, said rectangle DEFG is cut until reaching approximately the line defined by points CH.

In an embodiment of the invention, the template shown in FIG. 6 or FIG. 7 is symmetrical relative to axis X and axis Y (axes not shown in the figures), wherein each axis passes through the geometric center of the template). In a further embodiment of the invention, the template shown in FIG. 6 or FIG. 7 is not symmetrical relative to axis X and axis Y, wherein each axis passes through the geometric center of the template.

Figure 8:
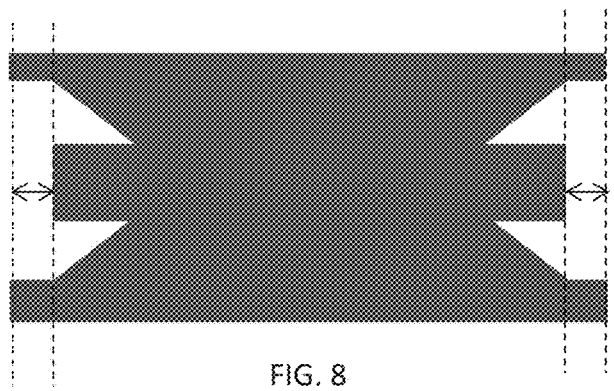
FIG. 8 shows an embodiment of the invention, wherein an additional cut is made, on each side, to the template shown in FIG. 7.

Therefore, as evident from FIG. 8, in which in addition to the cuts for forming the quadrilaterals 50B, said additional cut is made. In this regard, said cut enables the joining and folding of the sleeve to completely seal the sleeve, since said cut removes any surplus material. The depth of said cut, as evident from FIG. 8, depends on, and varies according to, approximately the location of line CH, with the location of CH+ being able to be either a constant and/or the length of line CD, wherein a complete sealing is achieved when distance CD is approximately the same distance as the sum of distances BC+DE (wherein DE may or may not be cut), such that when the respective joining is made, a complete sealing is achieved, thereby forming the reactor. Similar cuts are made in the embodiment shown in FIG. 6. Those skilled in the art will appreciate that angle Q and the spacing distance BE (the same applies to the other quadrilaterals 50B) between the quadrilateral parallel sides 50B, which in turn define the length of distance CD, may vary, either one or both, without affecting the subject matter of the present invention. In an embodiment of the invention, said spacing distance BE depends on the mechanical properties of the membrane material and on the capacity of the biodigester system 1. In an embodiment of the invention, the spacing distance BE is approximately 18%+10% the rectangular membrane width. In a particular embodiment of the invention, said angle Q is 75°+10°.

Figure 9:
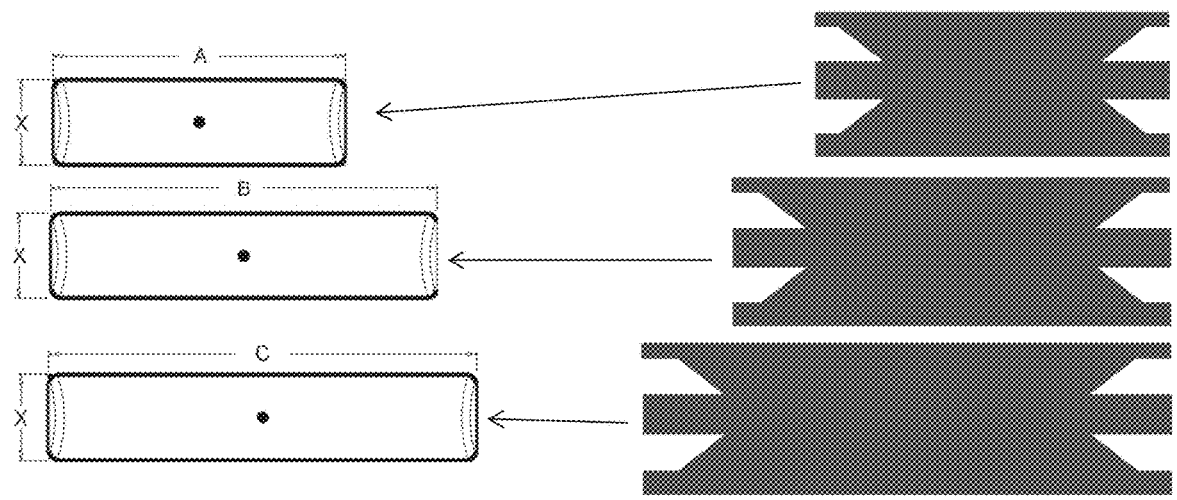
FIG. 9 shows an upper view of reactors with different capacities manufactured from templates preventing the creation of creases and in which it can be observed that the variant is the reactor body rather than the reactor ends.

FIG. 9 shows an upper view of reactors with different dimensions, wherein in an embodiment of the invention the width of each reactor is maintained, but the length of each reactor may vary according to each user's need. Thus, only the length of the respective template for forming the reactor is fitted.

Figure 10:
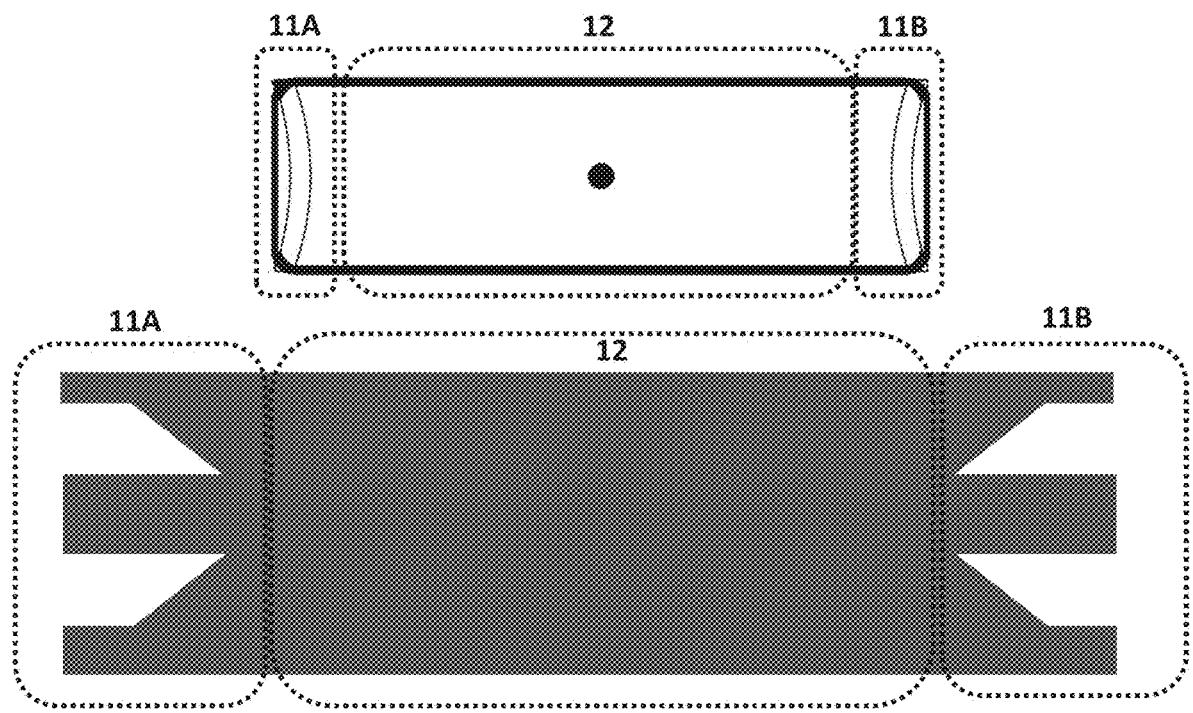
FIG. 10 shows an upper view of a final reactor and a template for the manufacture of said reactor, wherein said reactor is shown as being divided into at least three modules so that each one of said modules is manufactured in series with at least one particular template in accordance with an embodiment of the present invention.

FIG. 10 shows an embodiment of the invention, wherein reactor 10 is divided into three portions or segments, wherein each portion is formed by at least one template segment. Said portions are the reactor ends 11A and 11B, as well as the reactor body 12. Those skilled in the art will appreciate that the number of portions into which the reactor is divided may vary without affecting the subject matter of the present invention. Thus, in an embodiment of the invention, reactor ends 11A and 11B use at least one template, maintaining the crease-preventing design, and the reactor body 12 uses another type of template, preferably rectangular, said template may vary in length according to each user's need and the biodigester capacity 1, but maintaining the same diameter. Said at least one reactor end template 11A and/or 11B is joined to the reactor body template 12, such that there is a correspondence between said reactor end template 11A and/or 11B and the reactor body template 12, thereby defining a modular manufacturing of reactors. That is, the reactor ends 11A and/or 11B are manufactured separately and the reactor body 12 maintains a simple rectangular shape capable of subsequently forming the sleeve or pipe, such that the transportation to the place where the biodigester system is to be implemented is simpler.

Figure 11:
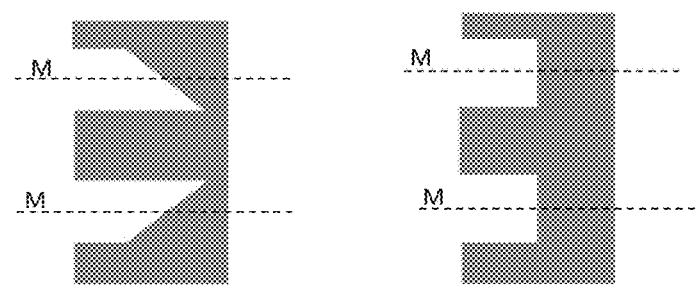
FIG. 11 shows the particular template or segment of the template corresponding to a reactor end in accordance with the division made in FIG. 10, either for the type of template of FIG. 6 or for the template of FIG. 7, and wherein the trapeze or rectangle mean can also be observed.

FIG. 11 shows the templates for the manufacture of the reactor ends in accordance with the embodiments shown in FIG. 6 and/or FIG. 7, wherein each quadrilateral means are also shown.

Figure 12:
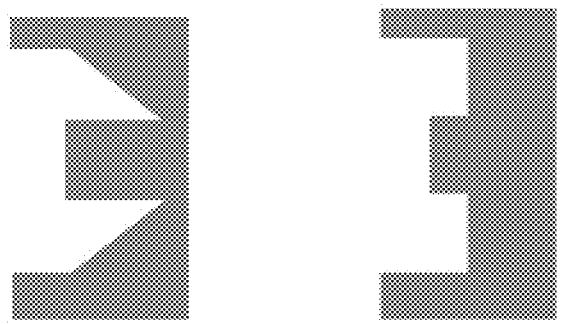
FIG. 12 shows an embodiment of the invention of the particular template or template segment, wherein an additional cut is being made to said template as compared with the template shown in FIG. 11.

FIG. 12 shows the template forming the reactor end in accordance with the embodiments shown in FIG. 6 or FIG. 7, wherein a rectangular portion is removed from said template as compared with templates of FIG. 11.

Moreover, a method for manufacturing biodigester reactors is disclosed, wherein the creation of creases is prevented when the reactor is inflated.

The membrane sleeve or plane pipe is a rectangular or partially rectangular membrane joined at a pair of opposite ends, said sleeve including an upper part and a lower part defined by the lines where folding of the plane membrane sleeve is made, being able to be different from the line of joining of the opposite ends. The lower part and the upper part having the same width and length. In this regard, said plain sleeve has a width X. As said sleeve is plain, the sleeve includes an upper part inner face in contact with the lower part inner face. Therefore, when the sleeve is inflated, a cylinder is formed, said cylinder having a 2× perimeter. Those skilled in the art will appreciate that the sleeve length (not specified in the figures) may vary without affecting the subject matter of the present invention. However, said length will determine the capacity of the biodigester system 1. Furthermore, those skilled in the art will appreciate that these measures are for ideal cases, since the final reactor product with gas and liquid waste inside said reactor will have a deformed shape or a shape similar to a circumference, wherein the heaviest waste will settle, deforming the lower part of the reactor and the biogas will tend to rise to accumulate at the upper part of the reactor.

Figure 13:
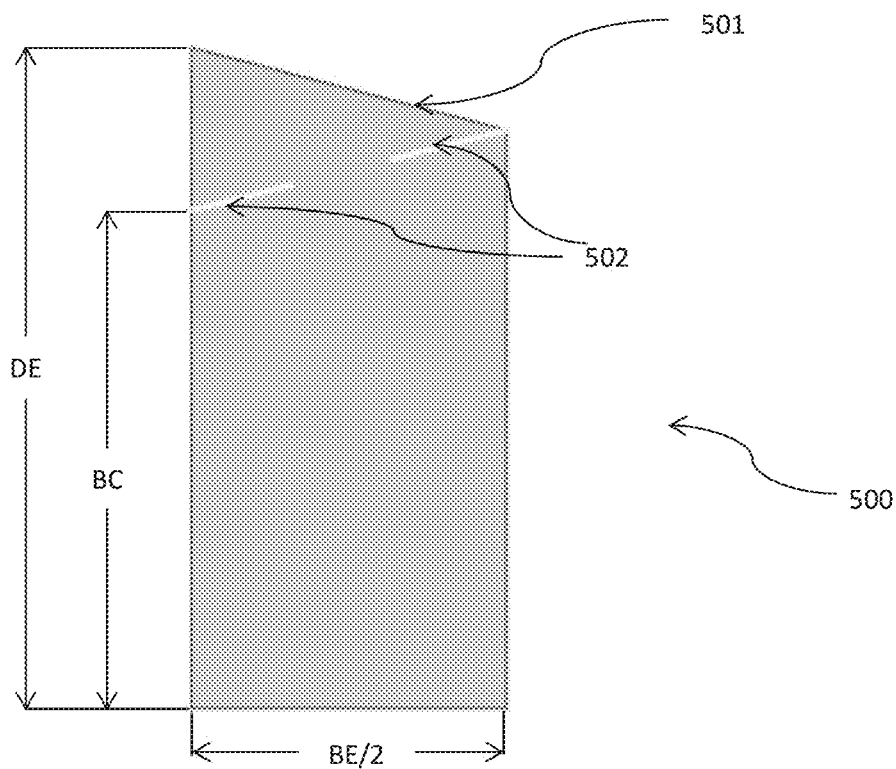
FIG. 13 shows an embodiment of a pattern to make cuts in a rectangular membrane sleeve to obtain a reactor or bag which prevents the creation of creases.

FIG. 13 shows a pattern 500 used to make pre-established cuts in a membrane sleeve or pipe so that said cuts may then be joined together to form the crease-preventing reactor. Those skilled in the art will appreciate that the dimensions of said pattern 500 may vary depending on the dimensions of the original rectangular template without affecting the subject matter of the present invention. Said pattern 500 is defined by a rectangular-shaped trapeze sheet including a greater height, a smaller height, a width, an angle, an upper slanted line 501, and a lower slanted line 502. Thus, an embodiment of the invention uses said pattern for the manufacture of the crease-preventing reactor.

In an embodiment of the invention, the width of pattern 500 ranges from 1% to 49% of the membrane sleeve or pipe width, with this value relying on the value of the mechanical properties of the membrane material.

In a preferred embodiment, the width of pattern 500 is approximately 18%+10% the width of the membrane sleeve or pipe (said pipe or sleeve being in a plain condition).

In an embodiment of the invention, the spacing distance between the quadrilateral parallel lines ranges from 1% to 49% the width of the rectangular template, with this value relying on the values of the mechanical properties of the membrane material. In a preferred embodiment, the spacing distance is approximately 18%+10% the width of the rectangular template.

In an embodiment of the invention, the length of at least one of the quadrilateral parallel lines ranges from 1% to 70% of the inflated sleeve diameter, with this value ideally relying on the mechanical properties of the membrane material. In a preferred embodiment, said length is approximately 60%+5% the diameter.

In an embodiment of the invention, the length of the longest height is approximately the same as the sum of the lengths of the upper slanted line 501 plus the lower slanted line 502.

Figure 14:
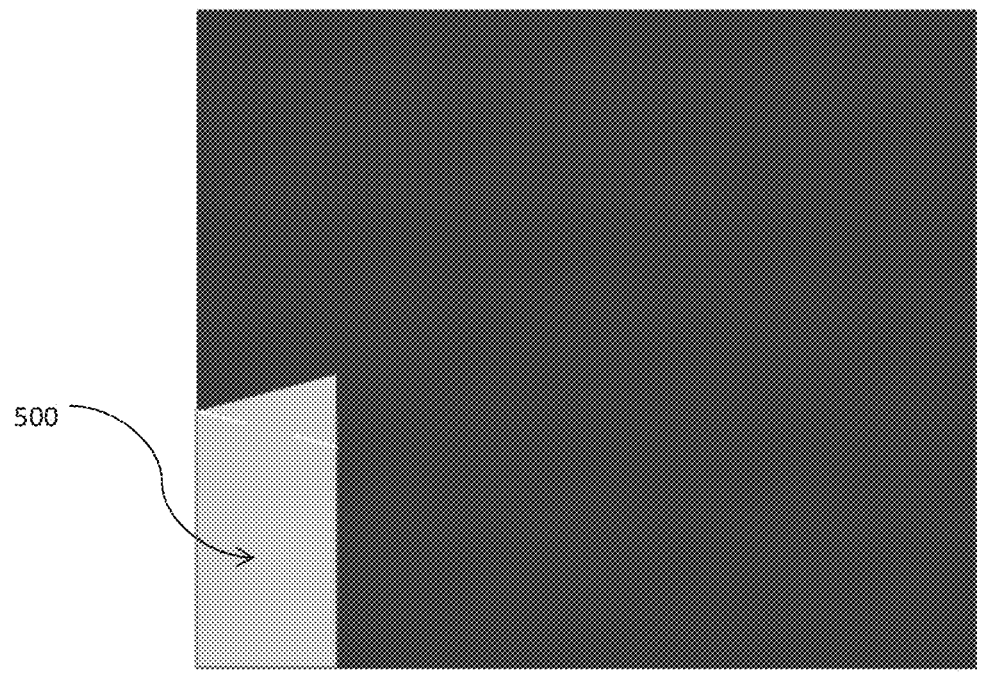
FIG. 14 shows in an upper view the location of the pattern on the rectangular sleeve in a corner of an end of said rectangular sleeve.

FIG. 14 shows the way in which pattern 500 is placed on a membrane pipe to make the cuts to form one of the quadrilaterals 50B (the same applies to the four corners of the membrane pipe). In this regard, a cut is made in the upper part of the membrane pipe, wherein said cut is made along the pattern longest height, said cut continues along the entire upper slanted line to the end of the pattern smallest height BC. Then, a cut is made in both parts of the membrane pipe, i.e. the upper layer and the lower layer, along the entire lower slanted line. Finally, a cut is made in the lower layer of the membrane pipe along the longest height line DE, from the smallest slanted line to the start of said longest height. Those skilled in the art will appreciate that the order or the way in which cuts are made by using pattern 500 may vary without affecting the subject matter of the invention.

Figure 15:
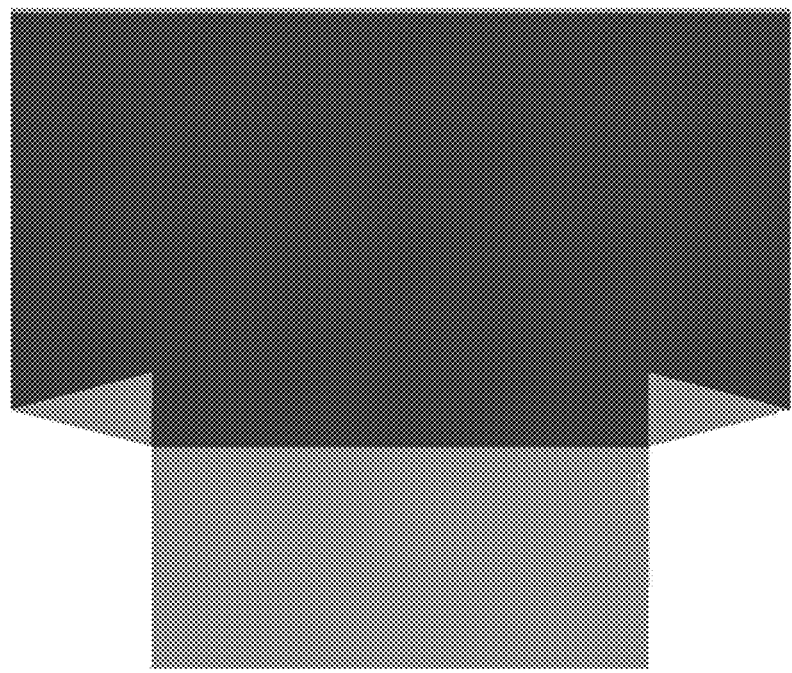
FIG. 15 shows in an upper view a rectangular sleeve end with the cuts made by using the pattern, one per each end corner and including an additional straight cut.

FIG. 15 shows a membrane pipe end, wherein cuts have been made with pattern 500 in both end corners, and wherein the additional cut shown in FIG. 8 is included.

In an embodiment of the invention, each reactor includes mechanical means allowing said reactor to be connected to at least another reactor, thereby defining a reactor with greater dimensions. Said connection may be made either in series and/or in parallel.

In an embodiment of the invention, the reactor is manufactured by using a material with resilient properties for facilitating handling, such as the performance of the folds, and for helping prevent the formation of creases.

In an embodiment of the invention, the filter uses organic matter fibers for filtering the biogas hydrogen sulfide. In an embodiment of the invention, said organic matter is coconut fiber.

In an embodiment of the invention, the joining technique relies on the material selected, but, in particular, the thermo-fusion technique is used. In an embodiment of the invention, a welding technique is used, wherein a filler material known in the art is provided, depending on the membrane material. In an embodiment of the invention, a thermo-fusion and/or welding technique is used. In this regard, those skilled in the art will appreciate that other joining and/or welding techniques may be applied to the present invention without affecting the subject matter thereof.

In an embodiment of the invention, the joining of line EF to the lines AB+IJ is performed by thermo-fusion.

In an embodiment of the invention, the joining of CD to DE is performed by extrusion or a welding where a filler material is provided.

In an embodiment of the invention, the biodigester system 1 further includes a biogas reservoir (not shown in the Figures), said biogas reservoir is coupled to the biogas outlet to collect the biogas produced by the biodigester system 1 and which has not yet been used. In an embodiment of the invention, the manufacture of said reservoir is performed from the templates and techniques disclosed herein.

Moreover, those skilled in the art will appreciate that the system reactor template of the present invention may include fittings requiring orifices and/or additional cuts without affecting the subject matter of the present invention, and which are not shown in said template. Said fittings may include, but are not limited to, inlet manhole, outlet manhole, and/or gas outlet, etc.

The preceding description of the various embodiments have been provided for illustration and description purposes only. Said description is not attempted to be exhaustive or to limit the present invention to those embodiments disclosed. Therefore, many modifications and variations will become evident to those skilled in the art. Moreover, the preceding disclosure is not attempted to limit the present invention.

The invention claimed is:

1. A method of manufacturing a biodigester reactor from a rectangular membrane template, the method comprising the steps of:
    making cuts, in a first pair of opposite ends of the rectangular template, for removal of membrane forming two quadrilaterals per said each opposite end, wherein each quadrilateral includes two first non-consecutive parallel sides and being also parallel to a second pair of opposite ends of the rectangular template and a third side being orthogonal to the two first non-consecutive parallel sides located over a corresponding edge of rectangular template, and wherein a spacing distance between said quadrilaterals is the same distance as the sum of the spacing distances between each quadrilateral and a closest end of the second pair of ends of the rectangular template;
    joining an edge of an end of the second pair of ends of the rectangular template to an edge of the other end of the second pair of ends of the rectangular template, thereby forming a sleeve;
    joining each fourth side of a quadrilateral to an adjacent side of a fourth side, such that an adjacent side of a quadrilateral is the closest side to an adjacent side of another quadrilateral, thereby partially sealing the sleeve; and
    joining remaining edges of the first pair of opposite ends, thereby totally sealing the sleeve.

2. The method according to claim 1, wherein one of the quadrilateral parallel sides has a longer length than the other side of the quadrilateral parallel sides, thereby defining a quadrilateral longer parallel side and a quadrilateral smaller parallel side, and further defining a fourth quadrilateral side not orthogonal to said parallel sides.

3. The method according to claim 2, wherein the longer parallel side has a length relying on mechanical properties of the membrane material.

4. The method according to claim 1, wherein at least one of the quadrilateral parallel sides has a length of 60%±5% the distance defined by a diameter forming the sleeve.

5. The method according to claim 1, wherein the method further includes the step of:
    making an additional cut, wherein said cut is straight and parallel to a distal end of the rectangular template, and wherein said cut is made between each quadrilateral longer side of each first end.

6. The method according to claim 1, wherein the quadrilateral parallel sides have the same length, thereby defining a fourth quadrilateral side being orthogonal to said parallel sides.

7. The method according to claim 1, wherein the spacing distance between the quadrilateral parallel sides relies on mechanical properties of the membrane material.

8. The method according to claim 1, wherein the spacing distance between the quadrilateral parallel sides is 18%±10% a spacing distance between the edges of the second pair of opposite sides of the rectangular template.

9. A membrane template for forming a biodigester reactor, said template, from a rectangular shape, includes:

cuts, in a first pair of opposite ends of a rectangular template, for removal of membrane forming two quadrilaterals per said each opposite end, wherein each quadrilateral includes two first non-consecutive parallel sides and being also parallel to a second pair of opposite ends of the rectangular template and a third side being orthogonal to the two first non-consecutive parallel sides located over a corresponding edge of rectangular template, and wherein a spacing distance between said quadrilaterals is the same distance as the sum of the spacing distances between each quadrilateral and a closest end of the second pair of ends of the rectangular template;

means for joining an edge of an end of the second pair ends of the rectangular template to an edge of the other end of the second pair of ends of the rectangular template, thereby forming a sleeve;

means for joining each fourth quadrilateral side to an adjacent side of a fourth side, such that an adjacent side of a quadrilateral is the closest side to an adjacent side of another quadrilateral, thereby partially sealing the sleeve; and means for joining remaining edges of the first pair of opposite ends, thereby totally sealing the sleeve.

10. The template in accordance with claim 9, wherein one of the quadrilateral parallel sides has a longer length than the other side of the quadrilateral parallel sides, thereby defining a longer quadrilateral parallel side and a smaller quadrilateral parallel side, and further defining a fourth quadrilateral side not orthogonal to said parallel sides.

11. The template in accordance with claim 10, wherein the longer parallel side has a length relying on mechanical properties of the membrane material.

12. The template in accordance with claim 9, wherein at least one of the quadrilateral parallel sides has a length of 60%±5% the distance defined by a diameter forming the sleeve.

13. The template in accordance with claim 9, wherein it further includes:

means for making an additional cut, wherein said cut is straight and parallel to a distal end of the rectangular template, and wherein said cut is made between each quadrilateral longer side of each first end.

14. The template in accordance with claim 9, wherein the quadrilateral parallel sides have the same length, thereby defining a fourth quadrilateral side being orthogonal to said parallel sides.

15. The template in accordance with claim 9, wherein the spacing distance between the quadrilateral parallel sides relies on mechanical properties of the membrane material.

16. The template in accordance with claim 9, wherein the spacing distance between the quadrilateral parallel sides is 18%±10% a spacing distance between the edges of the second pair of opposite ends of the rectangular template.

* * * * *